(12) United States Patent
Bougáret et al.

(10) Patent No.: US 6,864,246 B2
(45) Date of Patent: Mar. 8, 2005

(54) ANILIDE AND CYCLODEXTRIN COMPLEXES, THEIR PREPARATION AND THEIR USE AS MEDICINE IN PARTICULAR FOR TREATING DYSLIPIDEMIAE

(75) Inventors: Joël Bougáret, Francarville (FR); Elie Leverd, Castres (FR); Marie-Dominique Ibarra, Souilhanels (FR); Alexandre Gil, La Primaube (FR)

(73) Assignee: Pierre Fabre Medicament, Boulogne-Billancourt (FR)

(*) Notice: Subject to any disclaimer, the term of this patent is extended or adjusted under 35 U.S.C. 154(b) by 0 days.

(21) Appl. No.: 10/474,781

(22) PCT Filed: Apr. 9, 2002

(86) PCT No.: PCT/FR02/01224

§ 371 (c)(1),
(2), (4) Date: Oct. 10, 2003

(87) PCT Pub. No.: WO02/083632

PCT Pub. Date: Oct. 24, 2002

(65) Prior Publication Data

US 2004/0127462 A1 Jul. 1, 2004

(30) Foreign Application Priority Data

Apr. 10, 2001 (FR) .............................. 01 04855

(51) Int. Cl.[7] ............................................ A61K 31/715
(52) U.S. Cl. ........................... 514/58; 536/46; 564/218
(58) Field of Search ...................... 514/58; 536/46; 564/218

(56) References Cited

FOREIGN PATENT DOCUMENTS

EP          0 070 368 A1     1/1983
WO          97/19918 A1      6/1997

OTHER PUBLICATIONS

Oota et al. (JP 06219909) (Abstract Sent).*
Didier Junquero et al., "Pharmacological profile of F 12511, (S)–2',3', 5'–trimethyl–4'–hydroxy–α–dodecylthioacetanilide a powerful and systemic acylcoenzyme A: cholesterol acyltransferase inhibitor", Biochemical Pharmacology, 2001, pp. 97–108, vol. 61.
Shuichi Takamura et al., "Anticholesteremic ethyl α–(p–chlorophenoxy)isobutyrate–β–cyclodextrin compound", 6001 Chemical Abstracts, Mar., 11, 1975, vol. 83, No. 18, XP–002182063.

* cited by examiner

*Primary Examiner*—James O. Wilson
*Assistant Examiner*—Michael C. Henry
(74) *Attorney, Agent, or Firm*—Heller Ehrman White and McAuliffe LLP

(57) ABSTRACT

The invention concerns more particularly dodecylthio-phenylacetanilide derivative complexes such as (S)-2',3',5'-trimethyl-4'-hydroxy-α-dodecylthio-phenylacetanilide or related derivatives thereof and cyclodextrins.

20 Claims, 11 Drawing Sheets

Figure 1:
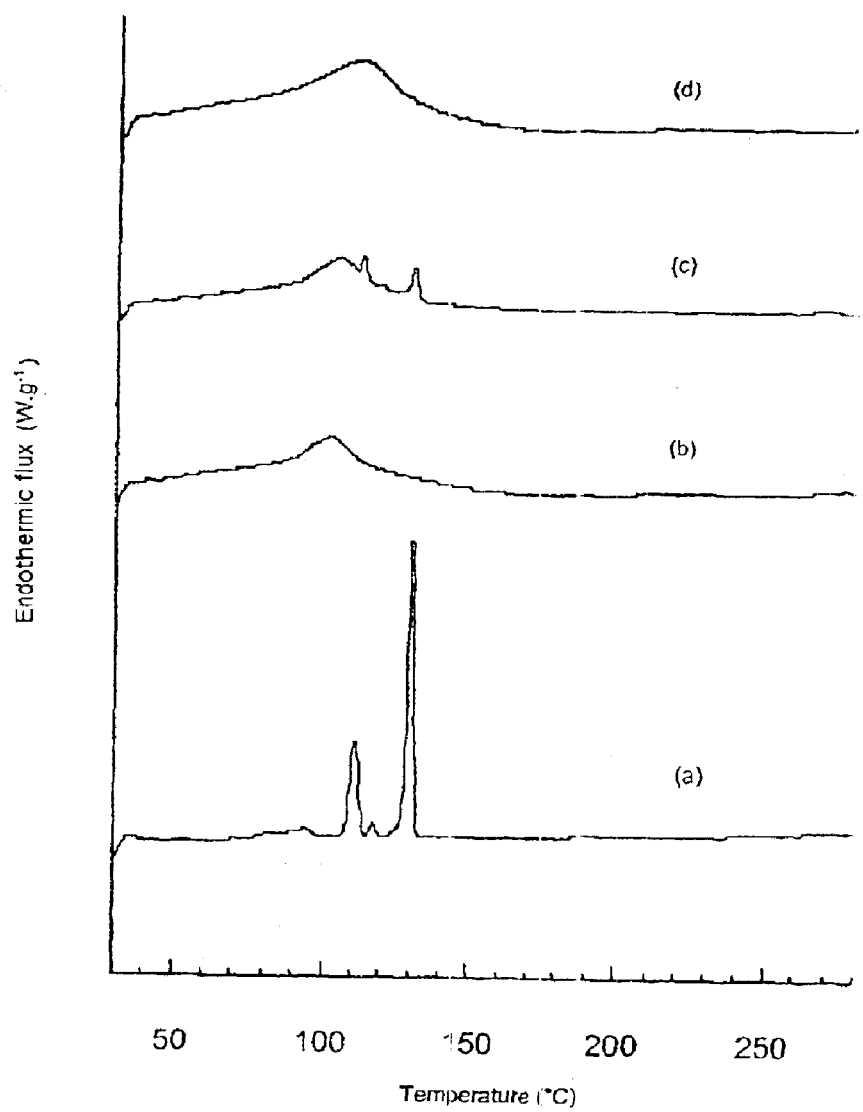

ANILIDE AND CYCLODEXTRIN COMPLEXES, THEIR PREPARATION AND THEIR USE AS MEDICINE IN PARTICULAR FOR TREATING DYSLIPIDEMIAE

This invention relates to complexes between polycarbon-chain anilide derivatives and cyclodextrins, and also to the pharmaceutical compositions containing them.

The polycarbon-chain anilide derivatives are more particularly dodecylthiophenylacetanilide derivatives, such as (S)-2',3',5'-trimethyl-4'-hydroxy-α-dodecylthiophenylacetanilide (laboratory code: F12511) or related derivatives thereof.

They are derivatives which are either crystalline, corresponding to a defined crystalline form or to a mixture of defined crystalline forms, or amorphous, i.e. with no particular crystalline form.

They are inhibitors of acyl cholesterol acyl transferase (or ACAT), an enzyme which catalyzes the esterification of free cholesterol, thus allowing intracellular storage of cholesterol, in the form of cholesterol linked to fatty acids.

They are molecules of choice for the treatment, of dyslipidemias, such as hypercholesterolemia, and the prevention of atherosclerosis.

F12511 is a non-salified molecule, of empirical formula $C_{29}H_{43}NO_2S$ and of molecular mass 479.73 g.

Its structural formula is:

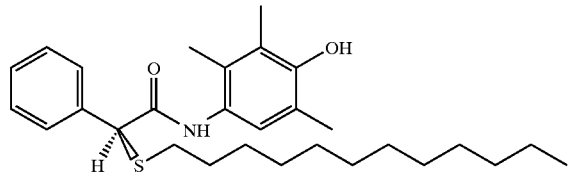

This molecule is virtually insoluble in water and the solvents which are usually used in pharmaceutical formation and physiologically compatible with essentially oral or parenteral administration.

By way of example, the table below gives some characteristic solubilities at saturation, at 25° C.:

| Solvent | Solubility at saturation expressed in mg/ml |
|---|---|
| Water | less than $50 \times 10^{-6}$[(1)] |
| Ethanol | 7 |
| Macrogol 400 | 1 |
| Corn oil | 0.3 |

[(1)]Limit of analytical detection

It is known, that hydrophilic solvents such as ethanol or Macrogol 400 cannot be used pure; unfortunately, adding water very rapidly causes the solubility of F12511 to decrease, as reflected by the result obtained with ethyl alcohol at 95%, where the solubility at saturation is no more than 2 mg/ml.

Finally, the use of surfactants in aqueous solution does not enable better results to be obtained. For example, the amount of F12511 solubilized after 2 hours of stirring in an aqueous solution containing 5% of sodium lauryl sulfate is approximately 10 μg/ml, at 25° C.

The cyclodextrins were discovered approximately one hundred years or so ago (Pr D. Duchene, F. Glomot and Dr C. Vaution Cyclodextrins and their industrial uses (Editions de Santé, 1987) Chapter 6: Pharmaceutical applications of cyclodextrins, p. 213). Initially, only small amounts of relatively impure cyclodextrins were isolated, but their high production cost prevented them being used industrially.

Recent progress in biotechnology has had the effect of considerably improving the production yield thereof, decreasing the cost of these materials and making possible the use of highly purified cyclodextrins or cyclodextrin derivatives.

Cyclodextrins come from the enzymatic degradation of starch, the two main constituents of which are: branched amylopectin and linear-chain amylose.

The partial degradation products of these two macromolecules are called dextrins.

Specific enzymes exist which not only degrade the macromolecules to smaller units (dextrins) but simultaneously also produce cyclic dextrins: cyclodextrins. These are cyclic oligosaccharide compounds which, depending on the reaction conditions, comprise mainly 6, 7 or 8 glucose units linked via α-(1,4) linkages: reference is then made to α-, β- and γ-cyclodextrin.

Native cyclodextrin molecules form toroidal structures, the outside of which is hydrophilic and the inside of which is hydrophobic. Their water-solubilities are, respectively, at 25° C.:

| | |
|---|---|
| α-cyclodextrin: | 14.2 g % ml, |
| β-cyclodextrin: | 1.8 g % ml, |
| γ-cyclodextrin: | 23.2 g % ml. |

Cyclodextrin derivatives have been prepared in order to increase this water-solubility. Hydroxypropyl-β-cyclodextrin and sulfobutyl ether β-cyclodextrin have a solubility of greater than 50 g % ml. Some methylated derivatives have a solubility also greater than 50 g % ml, such as heptakis(2,6-di-O-methyl)-β-cyclodextrin, or DIMEB, or even greater than 200 g % ml, such as the randomly methylated β-cyclodextrin derivative or RAMEB.

The exact value of the solubility depends on the degree of substitution of the cyclodextrin derivative considered.

This list is not limiting: the previous examples are given only to illustrate the possibilities of increasing the water-solubility of native cyclodextrins by preparing suitable derivatives which are clearly more soluble.

The present invention relates to complexes of polycarbon-chain anilide derivatives and of cyclodextrins, more particularly of dodecylthiophenylacetanilide derivatives, such as (S)-2',3',5'-trimethyl-4'-hydroxy-α-dodecylthiophenylacetanilide (F12511) or related derivatives thereof, and of cyclodextrins, more precisely of α-, β- and γ-cyclodextrins and derivatives thereof, such as hydroxypropyl, sulfobutyl ether or methylated derivatives.

These complexes are inclusion complexes or complexes formed by multiple interactions and, more generally, by surface interactions which can be observed in solid dispersions.

The complexes which are the subject of the invention made up of ACAT-inhibiting polycarbon-chain anilide derivatives and of cyclodextrins have a solubility in aqueous medium which is considerably greater than that of the polycarbon-chain anilide derivative alone.

Moreover, the capacity for micellization of the ACAT-inhibiting polycarbon-chain anilide derivatives, by surfactants such as sodium lauryl sulfate, is unexpectedly multiplied by a not insignificant factor in the presence of these complexes.

The polycarbon-chain anilide derivatives are amorphous or crystalline. In the latter case, this may be a single crystalline form or a mixture of various crystalline forms.

Four types of methods for preparing the active principle-:cyclodextrin complexes can be used. They differ from one another through the nature of the reaction medium: semi-solid, solid or liquid.

Type 1: In the case of semi-solid preparations, the active principle/cyclodextrin complexation is performed by kneading in the pasty state, in the presence of a small amount of liquid, most commonly of water, but also of ethanol, or of mixtures of water/ethanol, or any other suitable hydrophilic cosolvent.

The method may be a batch method (for example kneading in a suitable mixer), or continuous method (for example extrusion).

EXAMPLE 1

The kneading is carried out in a BRABENDER mixer. The tank of said mixer is equipped with a "Z"-shaped blade operated at 30 rpm. A mixture of 24.2 mmol of γ-cyclodextrin and 9.3 ml of purified water is introduced into the mixer tank and kneaded until a homogeneous paste is obtained. 5.7 g of F12511 (12.1 mmol) are gradually added and kneaded at between 30° C. and 55° C. until the endothermic peak characteristic of the solid/liquid transition of F12511 has completely disappeared. The product obtained is calibrated on a FREWITT oscillator and dried under vacuum at 40° C. for 12 hours.

It is characterized by:
Differential Thermal Analysis:

The differential thermal analysis is carried out by heating from 30° C. to 280° C. at 10° $C.min^{-1}$ under nitrogen using a Perkin Elmer DSC 7 device. The thermograms are given in FIG. 1. The thermogram for F12511 (a) shows three main characteristic endothermic events. The endothermic peak, centered over 102° C., of γ-cyclodextrin (b) corresponds to the evaporation of water. The thermogram for the simple physical mixture F12511:γ-cyclodextrin, under dry conditions, at the molar ratio (1:2) (c) is the simple superposition of the thermograms for the pure compounds. The F12511:γ-cyclodextrin system at the molar ratio (1:2) after kneading (d) shows a single endothermic peak centered over 112° C., the endothermic events characteristic of F12511 having completely disappeared.

Figure 2:
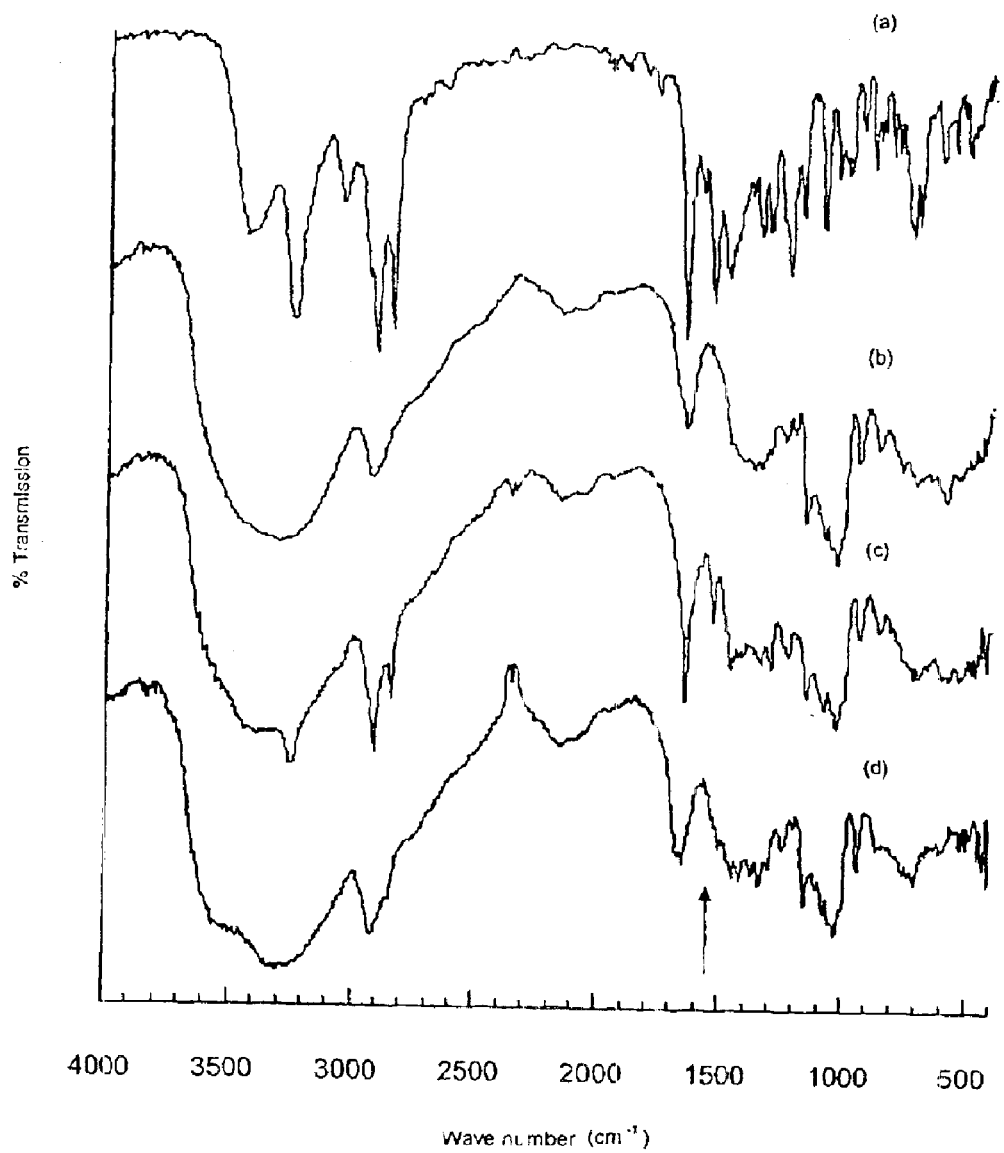

Fourier Transform Infrared (FTIR) Spectroscopy:

The infrared spectra are produced according to the KBr-dispersion method using a Nicolet 310 FTIR spectrometer. FIG. 2 gives the IR spectra of the various systems, F12511 (a), γ-cyclodextrin (b). The spectrum of the simple physical mixture F12511:γ-cyclodextrin, under dry conditions, at the molar ratio (1:2) (c) is the simple superposition of the spectra of the pure compounds. The spectrum of the F12511:γ-cyclodextrin mixture at the molar ratio (1:2) after kneading (d) shows a clear change compared to that of the simple physical mixture, with, in particular, the disappearance of the band located between 1530 $cm^{-1}$ and 1540 $cm^{-1}$ characteristic of the deformation of the N—H bond of the amide group and of the valence vibration of the C=C bonds of the aromatic rings of the F12511.

After stirring for 2 hours in an aqueous solution of sodium lauryl sulfate at 5%, the amount of F12511 solubilized from the F12511:γ-cyclodextrin (1:2) complex is 560 μg/ml instead of 11 μg/ml for the F12511 alone.

The active principle:cyclodextrin molar ratio used is an important factor which conditions the degree of interaction between the two entities, as demonstrated in the following Examples 2 and 3:

EXAMPLE 2

The mixing is carried out under the same conditions as Example 1. Only the amounts of F12511 and of γ-cyclodextrin, calculated to obtain a 1:1 molar ratio, vary. The differential thermal analysis carried out on the product obtained indicates a percentage interaction in the region of 60%. The amount of F12511 solubilized in an aqueous solution of sodium lauryl sulfate at 5% is then only 385 μg/ml after stirring for 2 hours.

EXAMPLE 3

The kneading is carried out under the same conditions as Example 1. Only the amounts of F12511 and of γ-cyclodextrin, calculated to obtain a 1:1.5 molar ratio, vary. The differential thermal analysis carried out on the product obtained indicates a percentage interaction in the region of 80%. The amount of F12511 solubilized in an aqueous solution of sodium lauryl sulfate at 5% is then only 495 μg/ml after stirring for 2 hours.

Comment: In Examples 1 to 3, the method for preparing the complexes is carried out by forming a paste of γ-cyclodextrin with purified water beforehand, and then adding the F12511. Other methods of preparation can be envisioned. In particular, an alternative method may consist in premixing F12511 and γ-cyclodextrin and then adding purified water.

EXAMPLE 4

The kneading is carried out in a mortar.

Various F12511:methyl-β-cyclodextrin ratios are used, in this case 1:1, 1:2 and 1:3, in the presence of water. The mass of F12511 treated is of the order of 500 mg. After drying in an incubator at 120° C., for 30 minutes, the final products are characterized by differential thermal analysis on a Mettler Toledo Star $ System device.

Figure 3:
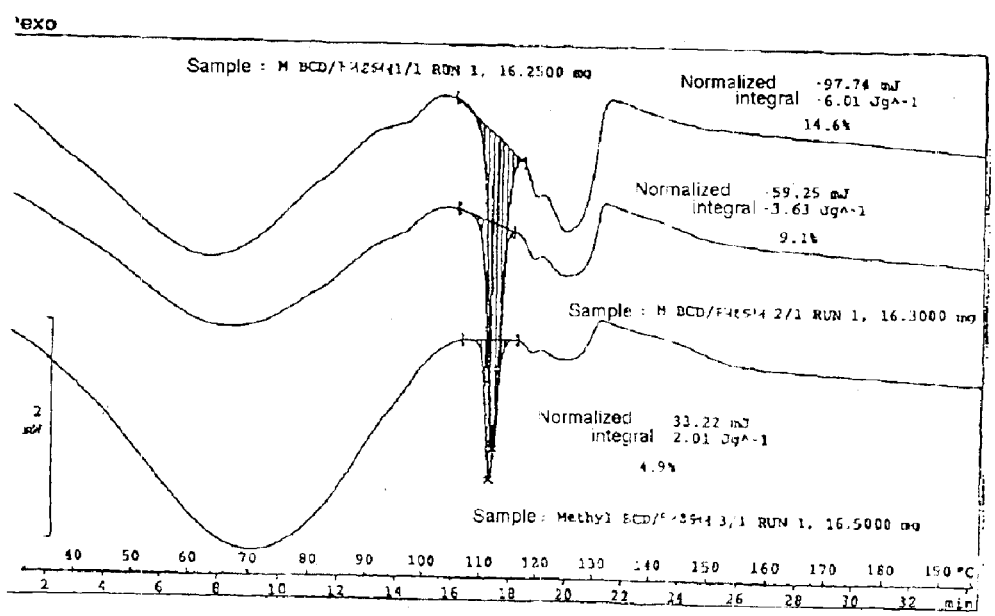

FIG. 3 indicates that, despite the drying performed, residual water remains present in the 3 compositions. The F12511 polymorphism peak is observed at 110° C., but the melting peak is absent. Only an endothermic and then exothermic unresolved peak ending at 150° C. is revealed. It is difficult to exploit the thermogram.

Figure 4:
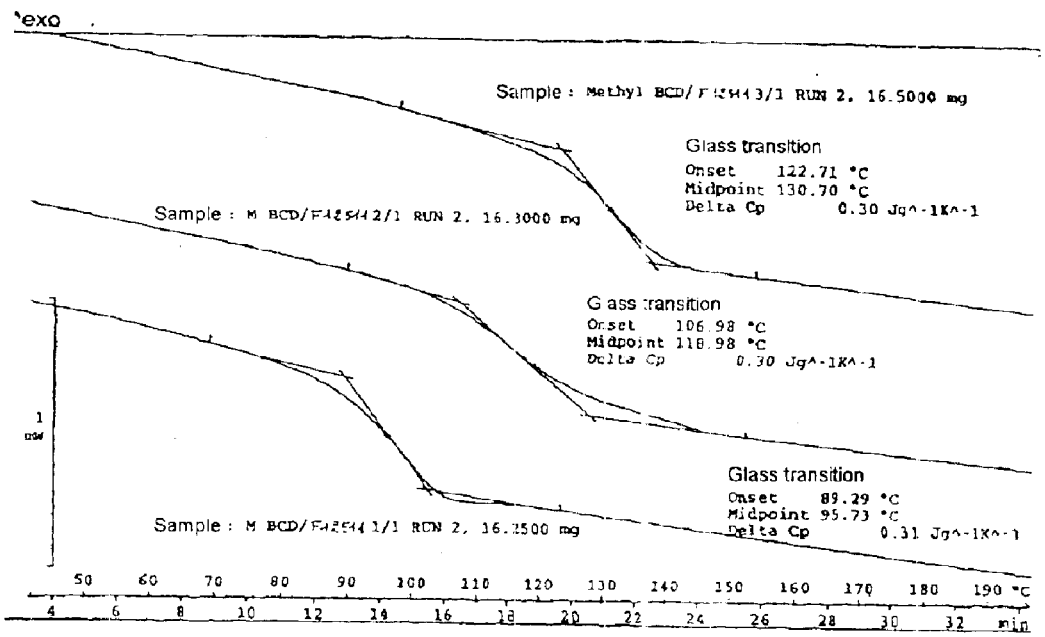

After cooling, a second differential thermal analysis is carried out (FIG. 4). No enthalpic effect is observed. Only a glass transition occurs, the temperature of which increases when the amount of methyl-β-cyclodextrin increases.

It is clearly apparent that the methyl-β-cyclodextrin interacts in a very exceptional manner with the F12511.

EXAMPLE 5

Example 1 concerns the preparation, in the presence of water, of an F12511:γ-cyclodextrin complex, at the 1:2 molar ratio, from a total mass of mixture of approximately 40 g.

It is essential to verify that this complex can be produced correctly, firstly, by changing scale, i.e. by increasing the batch size, and, secondly, by performing this change in scale on production devices for which models exist, both at the laboratory level and at the pilot and industrial levels, within the same homothetic range.

Z-blade mixers were used to do this.

By way of example two batches of almost 2 kg, i.e. 50 times 40 g, of complex were prepared by kneading on a WINKWORTH model 10Z mixer. The table below gives the production parameters used and the change in the amount of F12511 converted by interaction with γ-cyclodextrin over time, for a 1:2 molar ratio.

| Batch size (g) | Percentage of water in the mixture (%) | Temperature (° C.) | Rotation speed (rpm) | Change in the percentage of F12511 converted over time |
|---|---|---|---|---|
| 1979 | 25 | 35 | 20 | 10 min: 19% |
| | | | | 20 min: 65% |
| | | | | 30 min: 91% |
| | | | | 40 min: 95% |
| | | | | 50 min: 97% |
| | | | | 80 min: 97% |
| 1979 | 25 | 35 | 40 | 10 min: 33% |
| | | | | 20 min: 93% |
| | | | | 30 min: 96% |
| | | | | 40 min: 96% |
| | | | | 50 min: 98% |
| | | | | 80 min: 98% |

Figure 5:
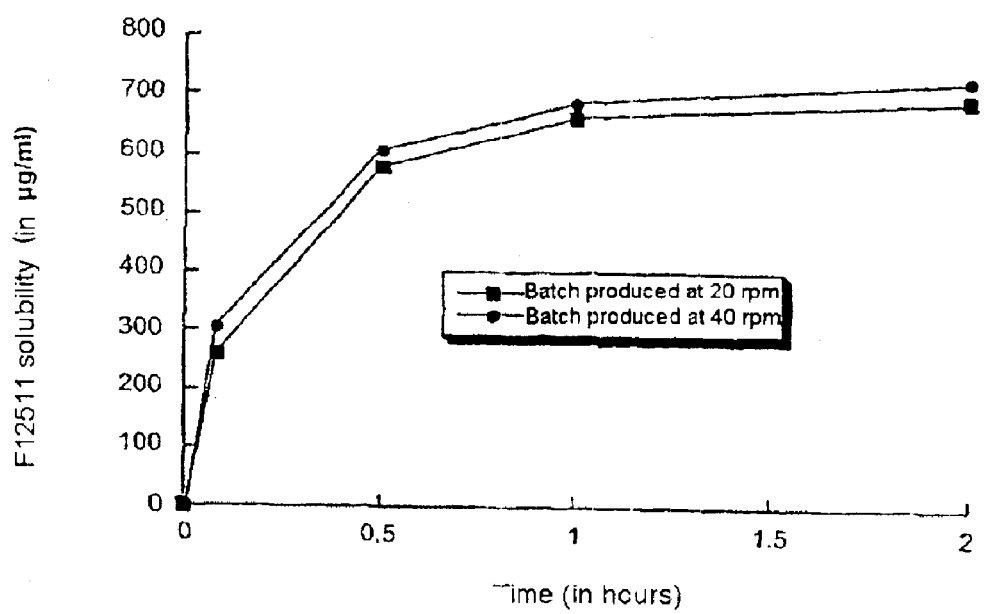

The kinetics for solubilization of these two batches in an aqueous solution of sodium lauryl sulfate at 5% are given in the table below and FIG. 5.

| Entity tested | Amount of F12511 solubilized in a solution of sodium lauryl sulfate at 5% (in µg/ml) | | | |
|---|---|---|---|---|
| | After 5 min | After 30 min | After 1 h | After 2 h |
| F12511:γ-cyclodextrin (1:2) Speed: 20 rpm | 258 | 579 | 663 | 698 |
| F12511:γ-cyclodextrin (1:2) Speed: 40 rpm | 307 | 608 | 686 | 731 |

Type 2: In solid medium, the active principle and the cyclodextrin are mixed in the pulverulent state and co-ground.

EXAMPLE 6

Co-grinding is carried out in a DANGOUMAU impact milling mill: 1 g of equimolar mixture consisting of 0.57 mmol of F12511 and 0.57 mmol of β-cyclodextrin is introduced into a 65 cm$^3$ steel pot containing an aluminum bead 20 mm in diameter and 10 g in mass. The pot is subjected to a vertical to-and-fro movement, at a frequency of 730 cycles per minute. The mixture is co-ground until the endothermic peak characteristic of the solid/liquid transition of the F12511 has completely disappeared.

Figure 6:
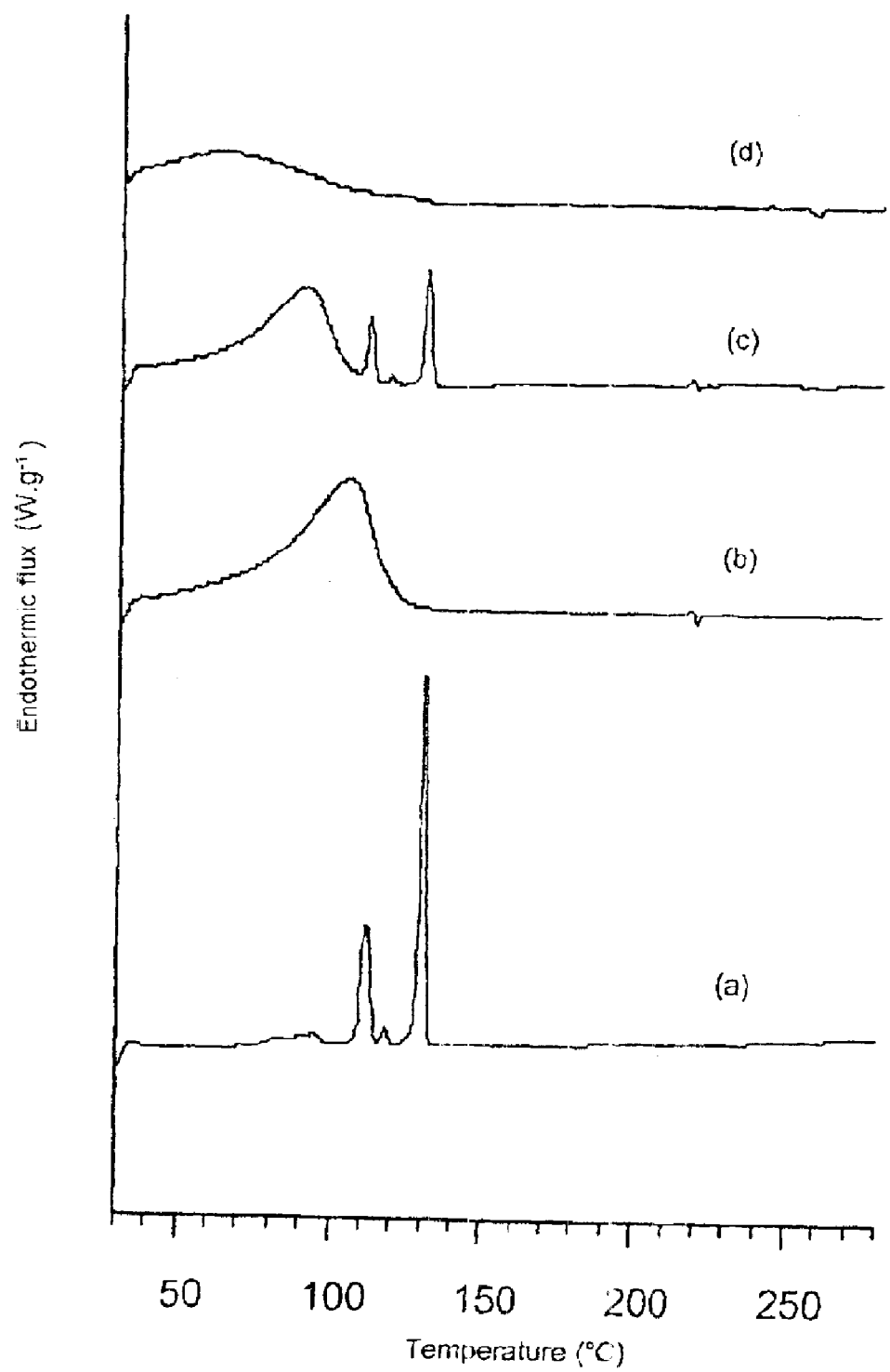

The product obtained is characterized by:
Differential Thermal Analysis:

The differential thermal analysis is carried out by heating from 30° C. to 280° C. at 10° C.min$^{-1}$ under nitrogen using a Perkin Elmer DSC 7 device. The thermograms are given in FIG. 6. The thermogram for F12511 (a) shows three main characteristic endothermic events. The endothermic peak centered over 105° C. of β-cyclodextrin (b) corresponds to the evaporation of water. The thermogram for the simple physical mixture F12511:β-cyclodextrin (c), under dry conditions, in equimolar proportions, is the simple superposition of the thermograms of the pure compounds. The co-ground equimolar mixture (d) shows a single endothermic peak centered over 70° C., the endothermic events characteristic of F12511 having completely disappeared.

Figure 7:
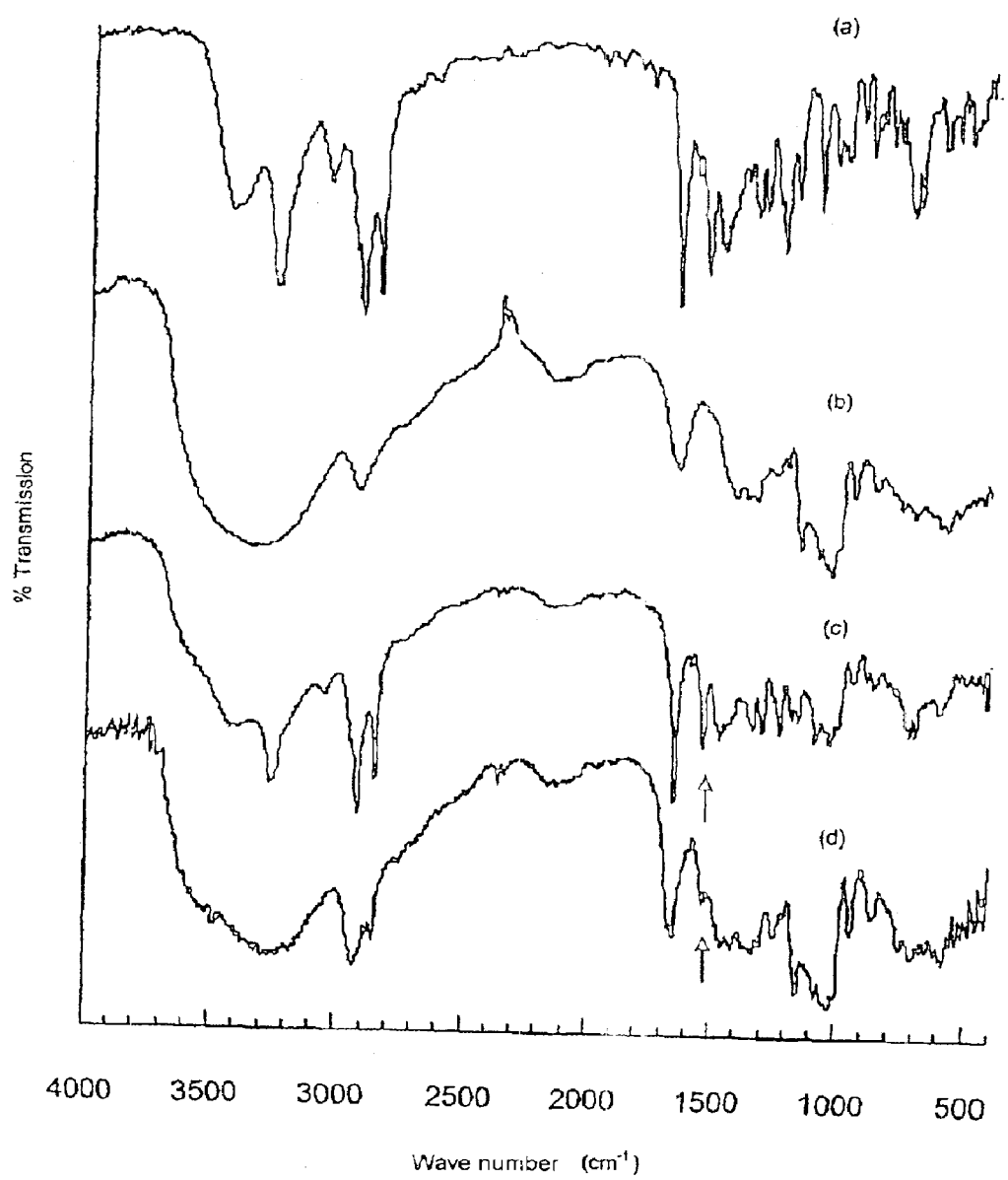

Fourier Transform Infrared (FTIR) Spectroscopy:

The infrared spectra are produced according to the KBr-dispersion method using a Nicolet 310 FTIR spectrometer. FIG. 7 gives the IR spectra of the various systems: F12511 (a), β-cyclodextrin (b). The spectrum for the equimolar physical mixture F12511:β-cyclodextrin (c) is the simple superposition of the spectra for the pure compounds. The spectrum for the co-ground equimolar mixture F12511:β-cyclodextrin (d) shows a clear change compared to that for the simple physical mixture: the disappearance of the band located between 1530 cm$^{-1}$ and 1540 cm$^{-1}$, characteristic of the deformation of the N—H bond of the amide group and of the valence vibration of the C=C bonds of the aromatic rings of the F12511, is in particular noted.

EXAMPLE 7

The co-grinding is carried out under the same conditions as Example 6.

The F12511:β-cyclodextrin mixture used corresponds to the molar ratio (1:2). It consists of 0.32 mmol of F12511 and 0.64 mmol of β-cyclodextrin.

This mixture is co-ground until the endothermic peak characteristic of the solid/liquid transition of F12511 has completely disappeared.

The differential thermal analysis and the Fourier Transform Infrared spectroscopy carried out on the final product show the absence of the free F12511.

The F12511:β-cyclodextrin complexes derived from the preparations described in the preceding Examples 6 and 7 were solubilized in an aqueous solution of sodium lauryl sulfate at 5%: after standing for 2 hours, the amounts of F12511 solubilized are, respectively, 420 and 210 µg/ml for the F12511:β-cyclodextrin molar ratios 1:1 and 1:2.

Examples 6 and 7 illustrate the preparation, by co-grinding, on a laboratory scale of F12511:β-cyclodextrin complexes with respective molar ratios of 1:1 and 1:2 for a total mass of 1 g.

The possibility of changing scale, and therefore of industrializing of the co-grinding process, was verified by using 1500 g of an F12511:β-cyclodextrin (1:2), mixture in a DM1 vibrating mill from the company SWECO, filled with 45 kg of milling medium.

Figure 8:
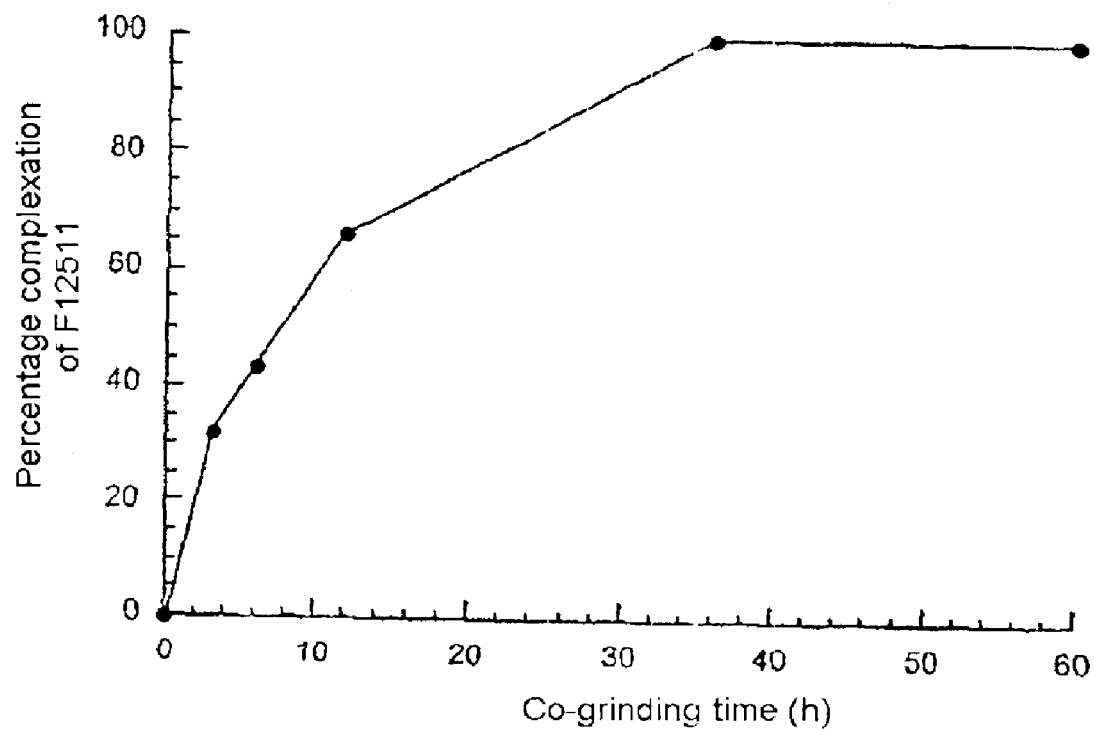

FIG. 8 shows the change in the percentage of complexation of F12511 during the co-grinding: conversion is complete for the sample taken after 36 h of treatment.

The above results clearly illustrate the possibility of complexing ACAT-inhibiting polycarbon-chain anilide derivatives and cyclodextrins using high energy co-grinding.

Other mills can also be used, in particular the Hybridizer system from the company NARA which uses powder surface modification technology (high energy impact or particle design mill) and which offers the advantage of a very short duration for the process.

EXAMPLE 8

Co-grinding is carried out in a Hybridizer system, model NHS-0.20 g of mixture consisting of 6.33 mmol of F12511and 12.66 mmol of β-cyclodextrin are introduced and co-ground at a rotation speed of 16200 rpm. After only 5 minutes of process, the product obtained already shows, by differential thermal analysis, a percentage of interaction of 75%.

After stirring for 2 hours in an aqueous solution of sodium lauryl sulfate at 5%, the amount of F12511 solubilized from this co-ground material is 105 µg/ml.

Type 3: In semi-solid or solid medium:

Independently of the physical nature of the reaction medium, the complexation of polycarbon-chain anilide derivatives with cyclodextrins occurs from the moment energy is introduced into the simple physical mixing of the two components, in the presence or absence of water, whether this energy is mechanical and/or thermal and/or developed by high pressures, as confirmed in the example below, which illustrates the combined action of a gentle mechanical energy with high temperatures and high pressures.

EXAMPLE 9

40 g of a mixture of F12511:γ-cyclodextrin, in a 1:2 molar ratio, containing 25% of water, are introduced into a stainless steel cylinder equipped with a sintered glass funnel at each end.

The F12511, as in the preceding examples, is generated chemically. This cylinder is placed in a high pressure autoclave preheated at 100° C.

Carbonic anhydride is introduced into the autoclave and pressurized at 300 bar.

After stabilization of the temperature and the pressure, two samples of mixture are taken after, respectively, 1 hour and 16 hours of complexation. They are ground and calibrated.

For the 1-hour sample, the differential thermal analysis reveals a degree of F12511:γ-cyclodextrin complexation of greater than 75%.

For the 16-hour sample, this degree of complexation is in the region of 95%. The solubilization kinetics thereof indicate a concentration of 520 µg/ml of solubilized F12511 after 2 hours of stirring in an aqueous sodium lauryl sulfate solution at 5%.

Type 4: The principle of the method of preparation in liquid medium is to bring the active principle and the cyclodextrin into contact, in the molecular state, and then to isolate the complex formed, for example using suitable solvents or non-solvents.

EXAMPLE 10

A mixture of 200 ml of water containing 1.47 mmol of β-cyclodextrin and of 400 ml of tetrahydrofuran containing 2.94 mmol of F12511 is stirred, by magnetic stirring, at 370 rpm, for a day, at a temperature of 40° C. After conservation at +5° C. for 3 days, a precipitate has formed, which precipitate is collected by filtration and dried. The amount of product recovered is 549.4 mg; it contains the F12511 complexed with the β-cyclodextrin.

Depending on their characteristics, the complexes are also recovered by co-crystallization, evaporation, lyophilization or nebulization.

The complexes of polycarbon-chain anilide derivatives and of cyclodextrins, more particularly of dodecylthiophenylacetanilide derivatives, such as (S)-2',3',5'-trimethyl-4'-hydroxy-α-dodecylthiophenylacetanilide or related derivatives thereof, and of native cyclodextrins or derivatives thereof, such as, respectively, α-, β-, γ-cyclodextrins or hydroxypropyl, sulfobutyl ether or methylated derivatives thereof, exhibit, surprisingly, solubilities in aqueous medium which are greatly greater than the solubilities of the initial polycarbon-chain anilide derivatives.

It is recalled that the solubility at saturation in water of F12511 is less than 50 ng/ml, this value in fact representing the limit of analytical detection of the molecule in saturated solution.

The kinetics for solubilization in water of the F12511:γ-cyclodextrin complex, at the molar ratio 1:2, show an amount of solubilized F12511 of between 1 and 2 µg/ml during the first two hours of stirring.

The use of γ-cyclodextrin therefore makes it possible to multiply the amount of F12511 solubilized in the water by a factor of at least 20 to 40 times.

Figure 9:
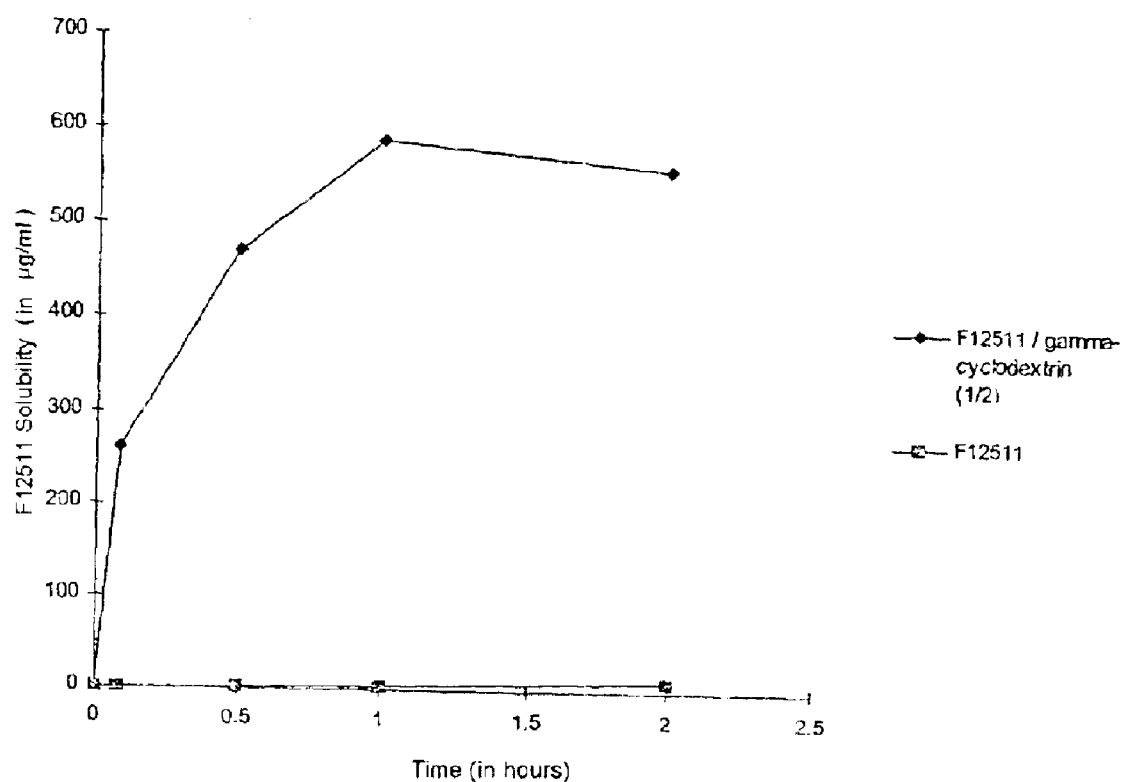

Moreover, the behavior of this same F12511:γ-cyclodextrin (1:2) complex in an aqueous solution of sodium lauryl sulfate at 5% reveals a micellization capacity for the surfactant which is multiplied up to 260 times compared to the result obtained for F12511 alone, as indicated in the table below and FIG. 9.

| Entity tested | Amount of F12511 solubilized in a solution of sodium lauryl sulfate at 5% (in µg/ml) | | | |
|---|---|---|---|---|
| | After 5 min | After 30 min | After 1 h | After 2 h |
| F12511 | 1 | 3 | 5 | 11 |
| F12511: γ-cyclodextrin (1:2) | 260 | 470 | 590 | 560 |

The results are just as surprising with the F12511:β-cyclodextrin complexes (1:1 and 1:2 molar ratios).

Figure 10:
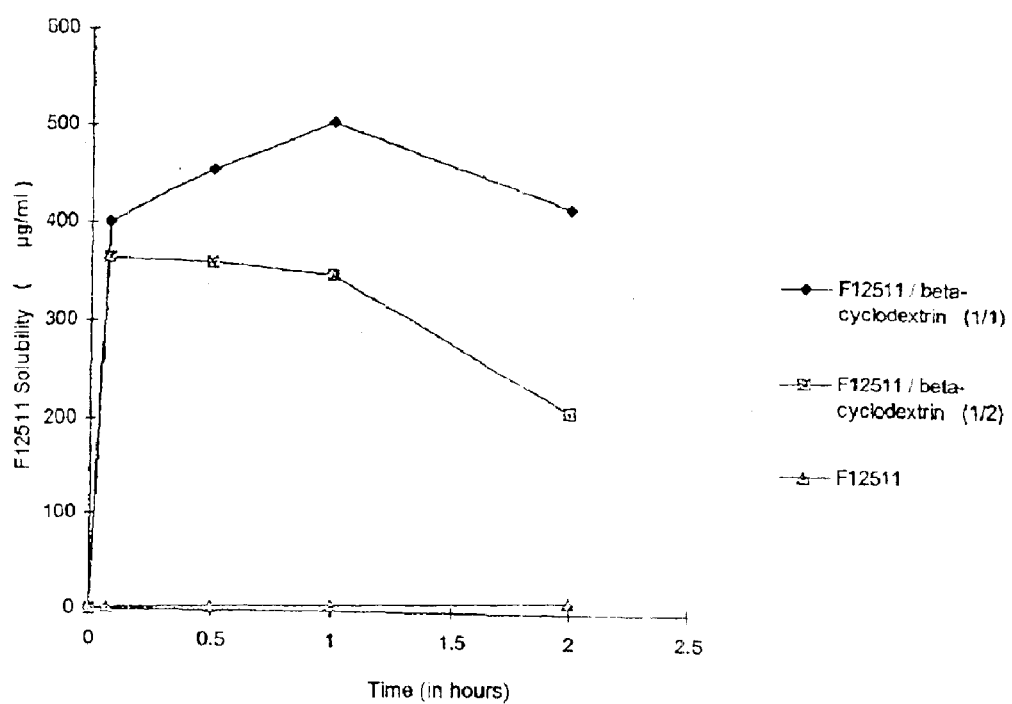

They are given in the table below and illustrated in FIG. 10.

| Entity tested | Amount of F12511 solubilized in a solution of sodium lauryl sulfate at 5% (in µg/ml) | | | |
|---|---|---|---|---|
| | After 5 min | After 30 min | After 1 h | After 2 h |
| F12511 | 1 | 3 | 5 | 11 |
| F12511: β-cyclodextrin (1:1) | 400 | 455 | 505 | 420 |
| F12511: β-cyclodextrin (1:2) | 365 | 360 | 350 | 210 |

The capacity for micellization of the F12511 by sodium lauryl sulfate can be multiplied up to 400 times compared to the result obtained for F12511 alone.

In the active principle:cyclodextrin complexes obtained, the molar ratios of the two entities are variable: they are advantageously between 1:5 and 5:1, more precisely between 1:1 and 1:3, and more particularly equal to 1:2.

The choice of the latter value is perfectly illustrated in the table below, which gives, for example, for F12511:γ-cyclodextrin ratios increasing from 1:1 to 1:2 by increments of 0.1 for the γ-cyclodextrin:

firstly, the percentage complexation of the F12511 determined by differential thermal analysis, secondly, the amount of F12511 solubilized in a solution of sodium lauryl sulfate at 5% after stirring for 2 h.

The method for preparing the complex is kneading in aqueous medium.

| F12511:γ-cyclodextrin molar ratio | % complexation of F12511 | Amount of F12511 solubilized in a solution of sodium lauryl sulfate at 5% after 2 h (in µg/ml) |
|---|---|---|
| 1:1 | 61% | 385 |
| 1:1.1 | 66% | 400 |
| 1:1.2 | 70% | 409 |
| 1:1.3 | 75% | 400 |
| 1:1.4 | 78% | 457 |
| 1:1.5 | 83% | 495 |
| 1:1.6 | 85% | 509 |
| 1:1.7 | 90% | 560 |
| 1:1.8 | 92% | 570 |
| 1:1.9 | 94% | 583 |
| 1:2 | 100% | 560 |

The increase in the rate of dissolution noted in aqueous medium, for polycarbon-chain anilide active principles belonging to SUPAC classes II and IV of the American Food and Drug Administration due to their low 20 solubility, and more specifically to class IV with regard to their low permeability through gastrointestinal tract membranes, suggests a better availability to the organism and, consequently, a better bioavailability, while at the same time decreasing inter- and/or intra-patient variations.

The addition of hydrophilic agents such as, by way of nonlimiting examples, cellulosic polymers (for example hydroxypropylmethylcellulose or hydroxyethylcellulose or alternatively carboxymethylcellulose), polyvinylpyrrolidone derivatives (for example crospovidone) or surfactants (for example polysorbate), capable of increasing the hydrophilicity of the preparation, is part of the invention and may further improve the rate of dissolution of the complexes formed or the stability of these complexes.

These polymeric and/or surfactant hydrophilic compounds are used during the actual complexation of the polycarbon-chain anilide derivatives and the cyclodextrins or derivatives thereof, or else are included as ingredients in the excipient formula of the corresponding pharmaceutical compositions.

EXAMPLE 11

Various amounts of polysorbate 80 (Tween 80) were added to approximately 40 g of F12511:γ-cyclodextrin mixture (1:2 molar ratio) subjected to the kneading process. This illustrates the simultaneous use of hydrophilic compounds, in particular of polysorbates, during the actual preparation of the complexes.

These amounts appear in the table below:

| Mass of F12511 (g) | Mass of γ-cyclodextrin (g) | Mass of water (g) | Mass of Tween 80 (g) | Percentage of Tween 80 in the mixture (%) |
|---|---|---|---|---|
| 5.68 | 34.34 | 9.41 | 0 | 0 |
| 5.66 | 34.34 | 9.33 | 0.08 | 0.16 |
| 5.67 | 34.38 | 9.41 | 0.25 | 0.50 |
| 5.67 | 34.32 | 9.42 | 0.51 | 1.00 |
| 5.66 | 34.34 | 9.39 | 0.98 | 2.00 |

The second table gives the percentages of complexation of the F12511, determined by differential thermal analysis, and also the amounts of F12511 solubilized, from these complexes, in water at 37° C. after stirring for 2 hours.

| Percentage of Tween 80 in the mixture (%) | Percentage of F12511 complexed (%) | Solubility of the F12511 in water, at 37° C., after 2 h (µg/ml) |
|---|---|---|
| 0 | 100 | 1.9 |
| 0.16 | 98 | 9.1 |
| 0.50 | 98 | 17.3 |
| 1.00 | 97 | 25.2 |
| 2.00 | 100 | 57.8[1] |

[1]Since the solubility of F12511 in water is less than $50 \times 10^{-6}$ mg/ml, a result of 57.8 µg/ml represents an increase in solubility of at least 1000-fold.

The use of polycarbon-chain anilide derivatives, more precisely of dodecylthiophenylacetanilide derivatives, such as (S)-2',3',5'-trimethyl-4'-hydroxy-α-dodecylthiophenylacetanilide or related derivatives thereof, the particles of which have a high specific surface area of between 0.5 and 100 m²/g, and more particularly between 5 and 50 m²/g, is also part of the invention.

The pharmaceutical compositions containing the complexes of polycarbon-chain anilide derivatives and of cyclodextrins, more particularly of dodecylthiophenylacetanilide derivatives, such as (S)-2',3',5'-trimethyl-4'-hydroxy-α-dodecylthiophenylacetanilide (F12511) or related derivatives thereof, and of cyclodextrins, more precisely α-, β-, γ-cyclodextrins and derivatives thereof, such as hydroxypropyl, sulfobutyl ether or methylated derivatives, are also part of the invention.

They are more particularly intended to be administered orally or parenterally. They are then, respectively, in the form of tablets, of gelatin capsules and of powders in sachets, of lyophilizates or of solutions, which are ready-to-use or are to be reconstituted extemporaneously.

With regard to the good results concerning the increases in water-solubility and the capacity for micellization in an aqueous solution containing 5% of sodium lauryl sulfate, obtained for F12511 via the F12511: cyclodextrin complexes compared to F12511 alone, it was decided to orally administer to dogs F12511 and the F12511:γ-cyclodextrin (1:2) complex prepared by kneading, each one being included in a gelatin capsule formulation, in order to verify whether or not the F12511 bioavailability was increased when this F12511 was complexed with cyclodextrins.

The characteristics of the gelatin capsules prepared are:

| | Reference formula F2 F12511 alone | Formula with F12511:γ-CD (1:2) |
|---|---|---|
| F12511 | 40.0 mg | 40.0 mg |
| Gamma-cyclodextrin | 0 | 241.9 mg[1] |
| excipients | qs 200.0 mg | qs 350.0 mg |
| | Per size 1 gelatin capsule | |

[1]Containing 8.67% of water.

The gelatin capsules were administered to 6 male dogs at a rate of one gelatin capsule orally.

Figure 11:
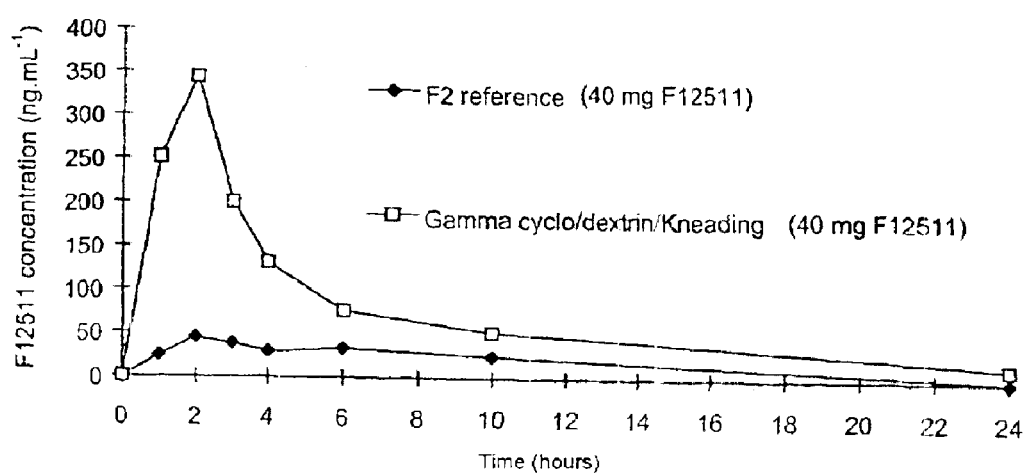

The mean plasma concentrations are represented in FIG. 11.

Comparisons of the areas under the curve indicate an area under the curve for the F12511:γ-CD (1:2) complex which is 8 times greater than that corresponding to the reference formula with the non-complexed F12511.

Moreover, the maximum plasma concentration reached for the F12511:γ-CD (1:2) complex is almost 10 times greater than that corresponding to the reference formula with the non-complexed F12511.

It is clear that the bioavailability of F12511, when given orally to dogs, is considerably increased when the F12511 is complexed with two moles of γ-cyclodextrin.

The pharmaceutical compositions which are the subject of the invention allow the treatment of dyslipidemias, such as hypercholesterolemia, and the prevention of atherosclerosis. Their method of action is essentially explained by inhibition of the enzyme acyl cholesterol acyltransferase or ACAT.

What is claimed is:

1. A complex comprising acyl cholesterol acyl transferase-(ACAT)-inhibiting dodecylthiophenylacetanilide derivatives and cyclodextrins.

2. The complex of claim 1 wherein the cyclodextrins are native cyclodextrins.

3. The complex of claim 2 wherein the dodecylthiophenylacetanilide derivatives: cyclodextrin molar ratios are between 1:5 and 5:1.

4. A method for preparing the complex of one of claims 1, 2, and 3, comprising supplying to the ACAT-inhibiting dodecylthiophenylacetanilide derivatives and the cyclodextrins a mechanical energy or thermal energy or energy developed by high pressures, or a combination thereof so as to effect complexation.

5. A pharmaceutical composition comprising the complex of one of claims 1, 2, and 3, in a form for oral or parenteral administration thereof.

6. The pharmaceutical composition of claim 5, further comprising hydrophilic compounds.

7. The pharmaceutical composition of claim 6, wherein the hydrophilic compounds are polymers selected from the group consisting of cellulose, polyvinylpyrrolidone derivatives, and surfactants.

8. The pharmaceutical composition as claimed in one of claim 6 or 7, wherein the dodecylthiophenylacetanilide derivative, the particles of which exhibit a high specific surface area of between 0.5 and 100 $m^2/g$.

9. The complex of claim 1, wherein said dodecylthiophenylacetanilide derivative is (S)-2',3',5'-trimethyl-4'-hydroxy-α-dodecylthiophenylacetanilide or related derivatives thereof.

10. The complex of claim 2, wherein said cyclodextrins are selected from the group consisting of γ-cyclodextrin, β-cyclodextrin, α-cyclodextrin and derivatives thereof.

11. The complex of claim 10, wherein said derivatives of the cyclodextrins are selected from the group consisting of hydroxypropyl, sulfobutyl ether and methylated derivatives.

12. The complex of claim 3, wherein the dodecylthiophenylacetanilide derivatives: cyclodextrin molar ratios are between 1:1 and 1:3.

13. The complex of claim 12, wherein the ratios are 1:2.

14. A method for preparing the pharmaceutical composition of claim 6, wherein said hydrophilic compounds are added during the complexation process.

15. A method for preparing the pharmaceutical composition of claim 6, wherein said hydrophilic compounds are added as an excipient after complexation.

16. The pharmaceutical composition of claim 7, wherein said surfactants are polysorbates.

17. The pharmaceutical composition of claim 8, wherein said surface area is between 5 and 50 $m^2/g$.

18. A method for preparing the complex of claim 1, comprising a process selected from the group consisting of:

(a) kneading the ACAT-inhibiting dodecylthiophenylacetanilide derivatives and cyclodextrins and cyclodextrins in a semi-solid medium continuously or in batches;

(b) grinding ACAT-inhibiting dodecylthiophenylacetanilide derivatives and cyclodextrins in a solid medium;

(c) mechanically combining ACAT-inhibiting dodecylthiophenylacetanilide derivatives and cyclodextrins in a semi-solid or solid medium at high temperatures and high pressures; and (d) co-precipitating ACAT-inhibiting dodecylthiophenylacetanilide derivatives and cyclodextrins in a liquid medium.

19. A method of treating dyslipidemiaes comprising administering to a subject in need thereof an effective amount of the pharmaceutical composition of claim 5.

20. The method of claim 19, wherein said dyslipidemia is hypercholesterolemia.

* * * * *